United States Patent
Huchel et al.

(10) Patent No.: US 9,845,449 B2
(45) Date of Patent: Dec. 19, 2017

(54) STABILIZED PERFUME OILS

(75) Inventors: Ursula Huchel, Cologne (DE);
Andreas Gerigk, Erkelenz (DE);
Hubert Smyrek, Krefeld (DE); Ralf Bunn, Duesseldorf (DE); Andreas Bauer, Kaarst (DE); Manuela Materne, Kaarst (DE); Marc Weyhe, Krefeld (DE); Klaus Intemann, Krefeld (DE); Dagmar Preis-Amberger, Leverkusen (DE)

(73) Assignee: Henkel AG & Co. KGaA (DE)

( * ) Notice: Subject to any disclaimer, the term of this patent is extended or adjusted under 35 U.S.C. 154(b) by 82 days.

(21) Appl. No.: 13/585,926

(22) Filed: Aug. 15, 2012

(65) Prior Publication Data

US 2012/0309669 A1   Dec. 6, 2012

Related U.S. Application Data

(63) Continuation of application No. PCT/EP2011/050252, filed on Jan. 11, 2011.

(30) Foreign Application Priority Data

Feb. 18, 2010  (DE) .................. 10 2010 002 106

(51) Int. Cl.
| | |
|---|---|
| *C11B 9/00* | (2006.01) |
| *C11D 3/50* | (2006.01) |
| *A61K 8/41* | (2006.01) |
| *A61L 9/01* | (2006.01) |
| *A61Q 13/00* | (2006.01) |
| *C11D 3/30* | (2006.01) |
| *C11D 7/32* | (2006.01) |
| *A61L 9/04* | (2006.01) |

(52) U.S. Cl.
CPC .................. *C11D 3/50* (2013.01); *A61K 8/41* (2013.01); *A61L 9/01* (2013.01); *A61Q 13/00* (2013.01); *C11D 3/30* (2013.01); *C11D 7/3218* (2013.01); *A61L 9/04* (2013.01)

(58) Field of Classification Search
CPC .... A61K 8/41; A61L 9/01; A61L 9/04; C11D 7/3218; C11D 3/30; C11D 3/50; A61Q 13/00
USPC ............................................................. 512/2
See application file for complete search history.

(56) References Cited

FOREIGN PATENT DOCUMENTS

| | | | |
|---|---|---|---|
| DE | 102006017879 A1 | 10/2007 | |
| EP | 0 137 173 A2 * | 8/1984 | ............ A61K 7/32 |
| EP | 1254651 A1 | 11/2002 | |
| EP | 1787689 A1 | 5/2007 | |
| EP | 2127632 A1 * | 12/2009 | |
| GB | 2422780 A * | 8/2006 | |
| GB | 2444702 A | 6/2008 | |
| JP | 2007300963 A * | 11/2007 | |

OTHER PUBLICATIONS

English Translation of JP 2007-300963 Obtained Nov. 18, 2014 at: http://www19.ipdl.inpit.go.jp/PA1/cgi-bin/PA1DETAIL.*
Partial English Translation of Table 2 of JP 2007-300963 Obtained Nov. 18, 2014 by Steven Spar, Foreign Translator, United States Patent & Trademark Office.*
Full English Translation of JP2007-300963. Obtained from the Translations Service Center at the United Stated Patent & Trademark Office on May 24, 2016.*
PCT International Search Report (PCT/EP2011/050252) dated Nov. 5, 2011.

* cited by examiner

*Primary Examiner* — Lanee Reuther
(74) *Attorney, Agent, or Firm* — David K. Benson

(57) ABSTRACT

Stable formulations and perfume compositions include amino alcohol(s) as well as >10 wt % fragrances.

9 Claims, No Drawings

STABILIZED PERFUME OILS

CROSS-REFERENCES TO RELATED APPLICATIONS

This application is a continuation of PCT/EP2011/050252, filed on Jan. 11, 2011, which claims priority under 35 U.S.C. §119 to DE 10 2010 002 106.7 filed on Feb. 18, 2010, both of which are hereby incorporated by reference.

FIELD OF THE INVENTION

The present invention generally relates to perfume compositions such as those used, for example, to perfume consumer products such as, for example, washing or cleaning agents or cosmetics, or those usable very generally for the generation of pleasant odors. The invention relates to a special perfume composition, to a method for stabilizing perfume oils, to a method for manufacturing perfumed consumer products, and to the use of a perfume composition in the manufacture of perfumed consumer products.

BACKGROUND OF THE INVENTION

A problem in the context of the handling of perfumes, fragrances, and fragrance mixtures is that their qualitative odor impression, as well as the intensity of the odor, usually change disadvantageously with time, for example as a result of environmental conditions, e.g. because of the influences of light, heat, oxygen, water, or protons. This instability of perfumes, fragrances, and fragrance mixtures is undesirable for obvious reasons, and a continuing need exists for perfumes having improved stability. This is also important, for example, in conjunction with the production-scale use of perfumes, fragrances, and fragrance mixtures in industry, in which large quantities of perfumes, fragrances, and fragrance mixtures are handled, stored for long periods, and incorporated into a variety of products.

DE 10 2006 017879 A1 describes the use of flavonoids, such as e.g. rutin, as stabilizers for scents.

It is desirable to create particularly stable perfume compositions. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A perfume composition encompasses amino alcohol(s) as well as >10 wt % fragrances. A perfume composition of this kind exhibits very good shelf stability, and is robust with respect to external influences such as, for example, heat.

A method for stabilizing perfume oil(s), includes adding 0.001 to 30 wt %, by preference 0.1 to 10 wt %, in particular 1 to 5 wt % amino alcohol to the perfume oil(s).

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

In addition to the fragrances and amino alcohol(s), the perfume composition can also by preference contain adjuvants, such as in particular solvents. Suitable solvents are, in particular, benzyl alcohol, dipropylene glycol, Dowanol, ethanol, isopropanol, isopropyl myristate, paraffin, propylene glycol, castor oil, and/or triazine. Usual stabilizers such as, for example, UV absorbers (e.g. benzotriazoles), quenchers, antioxidants (e.g. hindered phenols, lactone grades, and hydroperoxide grades), and chelating agents can also, for example, be contained as adjuvants. Other suitable adjuvants are, for example, complexing agents.

According to a preferred embodiment of the invention, the amino alcohol encompasses a compound according to formula (I)

HO—CR1R2CR3R4-NHR5      (I), where in said formula the residues R1, R2, R3, R4, and R5, mutually independently in each case, denote hydrogen or (optionally substituted) hydrocarbon residues (in particular hydroxyalkyl residues). The hydrocarbon residue can be linear or branched, substituted or unsubstituted.

It is particularly preferred if the perfume composition according to the present invention encompasses amino alcohol according to formula (II),

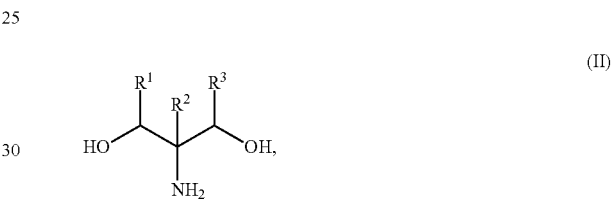

where in said formula the residues $R^1$, $R^2$, and $R^3$, mutually independently in each case, denote hydrogen or (optionally substituted) hydrocarbon residues (in particular hydroxyalkyl residues). The hydrocarbon residue can be linear or branched, substituted or unsubstituted.

Particularly preferred amino alcohols are, for example, 2-aminopropane-1,3-diol, 2-amino-2-(hydroxymethyl)propane-1,3-diol, 1-(methylamino)deoxy-D-glucite, as well as D-glucosamine, 2-amino-2-methylpropane-1,3-diol, 2-amino-2-ethylpropane-1,3-diol, and 1-phenyl-2-aminopropane-1,3-diol.

According to a further embodiment of the invention, it is possible for the amino alcohol contained in the perfume composition according to the present invention to be polymer-bound, i.e. in formula (I) at least one of the residues R1, R2, R3, R4, R5 would then be a polymeric hydrocarbon residue, resp. in formula (II) at least one of the residues R1, R2, R3 would be a polymeric hydrocarbon residue.

It is particularly preferred for purposes of the present invention if a high fragrance content is implemented in the perfume composition according to the present invention, so that it advantageously contains >15 wt %, >20 wt %, >25 wt %, >30 wt %, >35 wt %, >40 wt %, >45 wt %, >50 wt %, >55 wt %, or >60 wt %, by preference >70 wt %, advantageously >80 wt %, in particular >90 wt %, for example 95 wt % fragrances.

In usual fragrance mixtures, those fragrances that carry reactive functional groups, for example aldehydes, ketones, alcohols, and amines, are particularly unstable. Such fragrances are therefore often used only in subordinate quantities. Our invention, on the other hand, also enables the use of fragrance aldehydes, ketones, alcohols, and amines in larger quantities, with no need to accept decreases in quality, for example, during extended storage. Accordingly, in accordance with a preferred embodiment of the invention more than 1 wt %, advantageously more than 5 wt %, in particular more than 10 wt %, e.g. more than 15, 20, or 25 wt % of the fragrances contained are selected from those fragrances that carry an aldehyde function (RCH=O), a keto group (RR'C=O), a hydroxyl function (—OH), and/or groups having isolated double bonds, the "wt %" indication referring to the total quantity of fragrances contained.

According to a further preferred embodiment of the invention, a perfume composition according to the present invention is notable for the fact that at least one scent aldehyde, selected from adoxal, anisaldehyde, cymal, ethyl vanillin, florhydral, helional, heliotropin, hydroxycitronellal, koavon, lauraldehyde, lyral, methylnonylacetaldehyde, P-T-bucinal, phenylacetaldehyde, undecylenealdehyde, vanillin, 2,6,10-trimethyl-9-undecenal, 3-dodecen-1-al, alpha-n-amylcinnamaldehyde, 4-methoxybenzaldehyde, benzaldehyde, 3-(4-tert-butylphenyl)propanal, 2-methyl-3-(para-methoxyphenyl)propanal, 2-methyl-4-(2,6,6-trimethyl-2(1)-cyclohexen-1-yl)butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzylaldehyde, 1,2,3,4,5,6,7,8-octahydro-8,8-dimethyl-2-naphthaldehyde, 2,4-dimethyl-3-cyclohexene-1-carboxaldehyde, 2-methyl-3-(isopropylphenyl)propanal, 1-decanal, decylaldehyde, 2,6-dimethyl-5-heptenal, 4-(tricyclo[5.2.1.0 (2,6)]-decylidene-8)-butanal, octahydro-4,7-methane-1H-indenecarboxaldehyde, 3-ethoxy-4-hydroxybenzaldehyde, para-ethyl-alpha,alpha-dimethylhydrocinnamaldehyde, alpha-methyl-3,4-(methylenedioxy)hydrocinnamaldehyde, 3,4-methylenedioxybenzaldehyde, alpha-n-hexylcinnamaldehyde, m-cymene-7-carboxaldehyde, alpha-methylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexenecarboxaldehyde, 1-dodecanal, 2,4-dimethylcyclohexene-3-carboxaldehyde, 4-(4-hydroxy-4-methylpentyl)-3-cylohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert-butyl)propanal, dihydrocinnamaldehyde, 1-methyl-4-(4-methyl-3-pentenyl)-3-cyclohexene-1-carboxaldehyde, 5- or 6-methoxyhexahydro-4,7-methane indane-1- or -2-carboxaldehyde, 3,7-dimethyloctan-1-al, 1-undecanal, 10-undecen-1-al, 4-hydroxy-3-methoxybenzaldehyde, 1-methyl-3-(4-methyl-pentyl)-3-cyclohexenecarboxaldehyde, 7-hydroxy-3,7-dimethyloctanal, trans-4-decenal, 2,6-nonadienal, para-tolylacetaldehyde, 4-methylphenylacetaldehyde, 2-methyl-4-(2,6,6-trimethyl-1-cyclohexen-1-yl)-2-butenal, ortho-methoxycinnamaldehyde, 3,5,6-trimethyl-3-cyclohexenecarboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methane indane-1-carboxaldehyde, 2-methyloctanal, alpha-methyl-4-(1-methylethyl)benzeneacetaldehyde, 6,6-dimethyl-2-norpinene-2-propionaldehyde, para-methylphenoxyacetaldehyde, 2-methyl-3-phenyl-2-propen-1-al, 3,5,5-trimethylhexanal, hexahydro-8,8-dimethyl-2-naphthaldehyde, 3-propylbicyclo[2.2.1]-hept-5-ene-2-carbaldehyde, 9-decenal, 3-methyl-5-phenyl-1-pentanal, methylnonylacetaldehyde, hexanal, trans-2-hexenal, 1-p-menthene-q-carboxaldehyde, or mixtures thereof, is contained as a fragrance. By preference, at least 2, 3, 4, or 5 of the aforementioned scent aldehydes are contained. By preference, in accordance with a preferred embodiment of the invention, more than 1 wt %, advantageously more than 5 wt %, in particular more than 10 wt %, e.g. more than 15, 20, or 25 wt % of the fragrances contained in the perfume composition are scent aldehydes, in particular those as recited above.

A preferred embodiment of the invention likewise exists if at least one scent ketone selected from buccoxime; isojasmone; methyl-beta-naphtyl ketone; musk indanone; Tonalide/Musk Plus; alpha-damascone, beta-damascone, delta-damascone, isodamascone, damascenone, damarose, methyldihydrojasmonate, menthone, carvone, camphor, fenchone, alpha-ionone, beta-ionone, gamma-methyl (so-called) ionone, fleuramone, di-hydrojasmone, cis-jasmone, iso-E-Super®, methylcedrenyl ketone or methylcedrylone, acetophenone, methylacetophenone, para-methoxyacetophenone, methyl-beta-naphtyl ketone, benzylacetone, benzophenone, para-hydroxyphenylbutanone, celery ketone or livescone, 6-isopropyldecahydro-2-naphthone, dimethyloctenone, frescomenthe, 4-(1-ethoxyvinyl)-3,3,5,5-tetramethylcyclohexanone, methylheptenone, 2-(2-(4-methyl-3-cyclohexen-1-yl)propyl)cyclopentanone, 1-(p-menthen-6(2)yl)-1-propanone, 4-(4-hydroxy-3-methoxyphenyl)-2-butanone, 2-acetyl-3,3-dimethylnorbornane, 6,7-dihydro-1,1,2,3,3-pentamethyl-4(5H)indanone, 4-damascol, dulcinyl or cassione, gelsone, hexylone, isocyclemone E, methylcyclocitrone, methyllavender ketone, orivone, para-tertiary butylcyclohexanone, verdone, delphone, muscone, neobutenone, plicatone, veloutone, 2,4,4,7-tetramethyloct-6-en-3-one, tetrameran, or mixtures thereof is contained as a fragrance in the perfume composition according to the present invention. By preference, at least 2, 3, 4, or 5 of the scent ketones recited above are contained. By preference, in accordance with a preferred embodiment of the invention, more than 1 wt %, advantageously more than 5 wt %, in particular more than 10 wt %, e.g. more than 15, 20, or 25 wt % of the fragrances contained in the perfume composition are scent aldehydes, in particular those as recited above.

It is also in accordance with a preferred embodiment of the invention if amino alcohol is contained in the perfume composition in quantities from 0.001 to 30 wt %, by preference 0.1 to 10 wt %, in particular 1 to 5 wt %. Suitable lower limits for the amino alcohol can also be 0.5 wt %, 1.5 wt %, or 2 wt %. Suitable upper limits for the amino alcohol can also be 25 wt %, 20 wt %, or 15 wt %.

The perfume composition according to the present invention can in principle contain all usual and known fragrances. Fragrances are known to the skilled artisan in a wide variety; the fragrances contained can be, for example fragrances of the following compound classes: terpenoids, pyrocatechol derivatives, phenol derivatives, other aromatics, aliphatics, alicycles, and heterocycles.

According to a further preferred embodiment, fragrances having scent notes of the green notes (e.g. hex-3-en-1-ol), citrus notes (e.g. citral), lavender notes (e.g. lavender oil), floral notes (e.g. geraniol, ionone), aldehyde notes (e.g. alkanals and C8 to C13 alken-1-als), chypre notes (e.g. labdanum), fougère notes (e.g. cumarin), herbal notes (e.g. eugenol), oriental and/or woody notes (e.g. santalol, cedrol), and/or leather resp. tobacco notes (e.g. muscone, ambra oxide, civet), can be contained, for example, in the perfume composition according to the present invention.

According to a further preferred embodiment, fragrances from the group encompassing fragrances of natural or synthetic origin, preferably more-volatile fragrances, higher-boiling fragrances, solid fragrances, and/or adherent fragrances can, for example, be contained.

An additional advantage of the invention is the fact that the perfume composition according to the present invention brings about a scent-intensifying effect, i.e. the scent impression on the scented object becomes more intense and lasts longer, in particular when utilized in conjunction with textile laundering or textile care.

Adherent fragrances that are usable in the context of the present invention are, for example, essential oils such as angelica oil, anise oil, arnica flower oil, basil oil, bay oil, bergamot oil, champaca flower oil, silver fir oil, silver fir cone oil, elemi oil, eucalyptus oil, fennel oil, fir needle oil, galbanum oil, geranium oil, gingergrass oil, guaiac wood oil, balsam gurjun oil, helichrysum oil, ho oil, ginger oil, iris oil, cajeput oil, calamus oil, chamomile oil, camphor oil, kanaga oil, cardamom oil, cassia oil, pine needle oil, balsam copaiva oil, coriander oil, curled peppermint oil, caraway oil, cumin oil, lavender oil, lemon grass oil, lime oil, tangerine oil, lemon balm oil, ambrette seed oil, myrrh oil, clove oil, neroli oil, niaouli oil, olibanum oil, orange oil, oregano oil, palmarosa oil, patchouli oil, balsam peril oil, petitgrain oil, pepper oil, peppermint oil, pimento oil, pine oil, rose oil, rosemary oil, sandalwood oil, celery oil, spike lavender oil, star anise oil, turpentine oil, thuja oil, thyme oil, verbena oil, vetiver oil, juniper berry oil, wormwood oil, wintergreen oil, ylang-ylang oil, ysop oil, cinnamon oil, cinnamon leaf oil, citronella oil, lemon oil, and cypress oil.

Higher-boiling resp. solid fragrances of natural or synthetic origin can, however, also be used in the context of the present invention. These compounds include the compounds recited below, as well as mixtures thereof: ambrettolide, <-amylcinnamaldehyde, anethole, anisealdehyde, anise alcohol, anisole, anthranilic acid methyl ester, acetophenone, benzyl acetone, benzaldehyde, benzoic acid ethyl ester, benzophenone, benzyl alcohol, benzyl acetate, benzyl benzoate, benzyl formate, benzyl valerate, borneol, bornyl acetate, <-bromostyrene, n-decylaldehyde, n-dodecylaldehyde, eugenol, eugenol methyl ether, eucalyptol, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrol, jasmone, camphor, carvacrol, carvone, p-cresol methyl ether, coumarin, p-methoxyacetophenone, methyl-n-amyl ketone, methylanthranilic acid methyl ester, p-methylacetophenone, methylchavicol, p-methylquinoline, methyl ®-naphthyl ketone, methyl-n-nonylacetaldehyde, methyl-n-nonyl ketone, muscone, ®-naphthol ethyl ether,®-naphthol methyl ether, nerol, nitrobenzene, n-nonylaldehyde, nonyl alcohol, n-octylaldehyde, p-oxyacetophenone, pentadecanolide, ®-phenylethyl alcohol, phenylacetaldehyde dimethyl acetal, phenylacetic acid, pulegone, safrole, salicylic acid isoamyl ester, salicylic acid methyl ester, salicylic acid hexyl ester, salicylic acid cyclohexyl ester, santalol, skatole, terpineol, thymene, thymol, ©-undelactone, vanillin, veratrumaldehyde, cinnamaldehyde, cinnamyl alcohol, cinnamic acid, cinnamic acid ethyl ester, cinnamic acid benzyl ester.

Included among the more-volatile scents are, in particular, the lower-boiling fragrances of natural or synthetic origin, which can be used alone or in mixtures. Examples of more-volatile scents are alkylisothiocyanates (alkyl mustard oils), butanedione, limonene, linalool, linalyl acetate and linalyl propionate, menthol, menthone, methyl-n-heptenone, phellandrene, phenylacetaldehyde, terpinyl acetate, citral, citronellal.

According to a preferred embodiment of the invention, the perfume composition according to the present invention is notable for the fact that it encompasses ≤15 wt %, by preference ≤5 wt %, in particular ≤1 wt % surfactants. The surfactant content can also be below 10 wt % or below 2 wt % or below 0.5 wt % or below 0.1 wt % or below 0.01 wt %.

If surfactants are contained (which is optional), a suitable minimum quantity can then be 0.001 wt %, "wt %" being based in each case on the total composition. For purposes of the invention, the term "surfactants" also covers the emulsifiers as surface-active substances. Emulsifiers usable in preferred fashion are ethoxylated fatty alcohols, e.g. C12-18 fatty alcohols having 5 EO (e.g. Dehydrol LT 5 from Cognis), ethoxylated triglycerides (e.g. Eumulgin HRE 40, Eumulgin HRE 60 from Cognis), sorbitan fatty acid esters, e.g. polyoxyethylene sorbitan fatty acid esters, e.g. polyoxyethylene sorbitan monolaurate (e.g. Tween 20 from Merck), as well as hydrogenated, ethoxylated castor oil (e.g. Cremophor RH 40 from BASF).

Particularly good results according to the present invention can be obtained if the perfume composition according to the present invention is made up at a proportion ≥50 wt %, by preference ≥70 wt %, in particular ≥80 wt % (for example ≥90, ≥95, ≥97, or ≥99 wt %) of the constituents perfume, solvent, and amino alcohol.

Particularly good results according to the present invention can also be obtained if the perfume composition according to the present invention is made up at a proportion ≥50 wt %, by preference ≥70 wt %, in particular ≥80 wt %, e.g. ≥90 wt % or ≥95 wt %, of the constituents perfume and amino alcohol.

The perfume composition according to the present invention is by preference liquid or gel-like. This corresponds to a preferred embodiment of the invention. It can also, however, be solid, but liquid or gel-like embodiments are definitely preferred.

A further subject of the invention is a method for stabilizing perfume oils in which 0.001 to 30 wt % amino alcohol (by preference 0.1 to 10 wt %, in particular 1 to 5 wt %) is added to the perfume oil. Regardless of the nature of the perfume oil, i.e. its material composition, the addition of amino alcohol to the perfume oil brings about stabilization of the latter and thus brings about, for example, improved shelf stability as well as improved robustness with regard to external influences such as, for example, heat, air, contaminants. Preferred amino alcohols have already been recited.

A further subject of the invention is a method for manufacturing perfumed consumer products (in particular washing or cleaning agents, cosmetics, air fresheners, adhesives), a perfume composition according to the present invention being added. The resulting consumer products produce a superior scent effect upon use, and are notable for particularly good shelf stability.

A further subject of the invention is thus the use of a perfume composition according to the present invention in the manufacture of perfumed consumer products in order to improve the shelf stability of the consumer product.

A further subject of the invention is the use of a perfume composition according to the present invention in the manufacture of perfumed washing, cleaning, or care-providing agents in order to prolong the scent effect of the washing, cleaning, or care-providing agent and/or to achieve a long-lasting fresh odor upon utilization of the washing, cleaning, or care-providing agent (in particular with regard to dry textiles after automatic textile laundering).

Consumer products that profit from incorporation of the perfume composition according to our present invention are, in particular, washing or cleaning agents, cosmetics, air fresheners, and adhesives. More stable products result in this context.

Such consumer products, such as in particular washing, care-providing, or cleaning agents, preferably contain at least one, by preference multiple, active components, in particular cosmetic components or components having washing, care-providing, and/or cleaning activity, advantageously selected from the group encompassing anionic surfactants, cationic surfactants, amphoteric surfactants, nonionic surfactants, acidifying agents, alkalizing agents, anti-creasing compounds, antibacterial substances, antioxidants, antiredeposition agents, antistatic agents, builder substances, bleaching agents, bleach activators, bleach stabilizers, bleach catalysts, ironing adjuvants, cobuilders, fragrances, shrinkage preventers, electrolytes, enzymes, color protectants, coloring agents, dyes, color transfer inhibitors, fluorescent agents, fungicides, germicides, odor-complexing substances, adjuvants, hydrotropes, rinse aids, complexing agents, preservatives, corrosion inhibitors, optical brighteners, perfumes, perfume carriers, luster agents, pH adjusting agents, proofing and impregnation agents, polymers, swelling and anti-slip agents, foam inhibitors, sheet silicates, dirt-repelling substances, silver protectants, silicone oils, UV protection substances, viscosity regulators, thickening agents, discoloration inhibitors, anti-gray agents, vitamins, and/or fabric softeners.

The quantities of the individual ingredients in the consumer products according to the present invention, such as in particular washing, care-providing, or cleaning agents, are aimed in each case toward the intended use of the relevant agent, and the skilled artisan is familiar with the orders of magnitude of the quantities of ingredients to be used, or can gather them from the relevant technical literature.

The surfactant content, for example, will be selected to be higher or lower depending on the intended use of the consumer products according to the present invention. For example, the surfactant content of, for example, washing agents is usually between 10 and 50 wt %, by preference between 12.5 and 30 wt %, and in particular between 15 and 25 wt %, while, for example, cleaning agents for automatic dishwashing usually contain, for example, between 0.1 and 10 wt %, by preference between 0.5 and 7.5 wt %, and in particular between 1 and 5 wt % surfactants.

Consumer products according to the present invention can in particular contain builder substances, surface-active surfactants, enzymes, bleaching agents, such as by preference organic and/or inorganic peroxygen compounds, peroxygen activators, water-miscible organic solvents, sequestering agents, electrolytes, pH regulators, thickeners, and further adjuvants such as soil release active substances, optical brighteners, anti-gray agents, color transfer inhibitors, foam regulators, and dyes.

The consumer products according to the present invention can contain surfactants; anionic surfactants, nonionic surfactants, and mixtures thereof, but also cationic surfactants, are appropriate in particular. Suitable nonionic surfactants are, in particular, ethoxylation and/or propoxylation products of alkyl glycosides and/or of linear or branched alcohols each having 12 to 18 carbon atoms in the alkyl portion and 3 to 20, by preference 4 to 10, alkyl ether groups. Also usable are corresponding ethoxylation and/or propoxylation products of N-alkylamines, of vicinal diols, of fatty acid esters and of fatty acid amides that correspond, in terms of the alkyl portion, to the aforesaid long-chain alcohol derivatives, and of alkylphenols having 5 to 12 carbon atoms in the alkyl residue.

Suitable anionic surfactants are, in particular, soaps, and those that contain sulfate or sulfonate groups having preferably alkali ions as cations. Usable soaps are preferably the alkali salts of the saturated or unsaturated fatty acids having 12 to 18 carbon atoms. Such fatty acids can also be used in incompletely neutralized form. Included among the usable surfactants of the sulfate type are the salts of the sulfuric acid semiesters of fatty alcohols having 12 to 18 carbon atoms, and the sulfatization products of the aforesaid nonionic surfactants having a low degree of ethoxylation. Included among the usable surfactants of the sulfonate type are linear alkylbenzenesulfonates having 9 to 14 carbon atoms in the alkyl portion, alkanesulfonates having 12 to 18 carbon atoms, and olefinsulfonates having 12 to 18 carbon atoms that are produced upon reaction of corresponding monoolefins with sulfur trioxide, as well as alpha-sulfofatty acid esters that are produced upon sulfonation of fatty acid methyl or ethyl esters.

Cationic surfactants are by preference selected from among the esterquats and/or the quaternary ammonium compounds (QACs) in accordance with the general formula $(R^I)(R^{II})(R^{III})(R^{IV})N^+ X^-$, in which $R^I$ to $R^{IV}$ denote identical or different $C_{1-22}$ alkyl residues, $C_{7-28}$ aralkyl residues, or heterocyclic residues, where two (or in the case of an aromatic incorporating bond such as in pyridine, even three) residues form, together with the nitrogen atom, the heterocycle (e.g. a pyridinium or imidazolinium compound), and $X^-$ denotes halide ions, sulfate ions, hydroxide ions, or similar anions. QACs can be manufactured by the reaction of tertiary amines with alkylating agents such as, for example, methyl chloride, benzyl chloride, dimethyl sulfate, dodecyl bromide, but also ethylene oxide. The alkylation of tertiary amines having a long alkyl residue and two methyl groups can be achieved particularly easily, and the quaternization of tertiary amines having two long residues and one methyl group can also be carried out using methyl chloride under mild conditions. Amines that possess three long alkyl residues or hydroxy-substituted alkyl residues have low reactivity, and are quaternized, for example, using dimethyl sulfate. Suitable QACs are, for example, benzalkonium chloride (N-alkyl-N,N-dimethylbenzylammonium chloride), benzalkon B (m,p-dichlorobenzyldimethyl-$C_{1-2}$ alkylammonium chloride), benzoxonium chloride (benzyldodecyl-bis(2-hydroxyethyl)ammonium chloride), cetrimonium bromide (N-hexadecyl-N,N-trimethylammonium bromide), benzetonium chloride (N,N-dimethyl-N-[2-[2-[p-(1,1,3,3-tetramethylbutyl)phenoxy]ethoxy]ethyl]benzylammonium chloride), dialkyldimethylammonium chlorides such as di-n-decyldimethylammonium chloride, didecyldimethylammonium bromide, dioctyldimethylammonium chloride, 1-cetylpyridinium chloride, and thiazoline iodide, as well as mixtures thereof. Preferred QACs are the benzalkonium chlorides having $C_8$ to $C_{22}$ alkyl residues, in particular $C_{12}$ to $C_{14}$ alkylbenzyldimethylammonium chloride.

"Esterquats" are to be understood here as, by preference, compounds of the general formula IV,

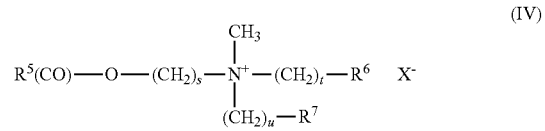

in which $R^5$ denotes an alkyl or alkenyl residue having 12 to 22 carbon atoms and 0, 1, 2, or 3 double bonds; $R^6$ and $R^7$, mutually independently, denote H, OH, or $O(CO)R^5$; s, t, and u, mutually independently in each case, denote the value 1, 2, or 3; and $X^-$ denotes an anion, in particular halide, methosulfate, methophosphate, or phosphate, as well as mixtures thereof. Compounds that contain the group O(CO) $R^5$ for $R^6$, and an alkyl residue having 16 to 18 carbon atoms for $R^5$, are preferred. Compounds in which $R^7$ additionally denotes OH are particularly preferred. Examples of compounds of formula (IV) are methyl-N-(2-hydroxyethyl)-N,N-di(tallowacyloxyethyl)ammonium methosulfate, bis(palmitoyl)ethylhydroxyethylmethylammonium methosulfate, or methyl-N,N-bis(acyloxyethyl)-N-(2-hydroxyethyeammonium methosulfate. If quaternized compounds of formula (IV) that comprise unsaturated groups are used, those acyl groups whose corresponding fatty acids have an iodine number between 5 and 80, by preference between 10 and 60, and in particular between 15 and 45, and/or that have a cis/trans isomer ratio (in mol %) greater than 30:70, by preference greater than 50:50, and in particular greater than 70:30, are preferred. Commercially usual examples are the methylhydroxyalkyldialkoyloxyalkylammonium methosulfates marketed by the Stepan company under the Stepantex® trademark, or the products of Cognis Deutschland GmbH known under the trade name Dehyquart® resp. the products of the manufacturer Goldschmidt-Wilco known under the name Rewoquat®.

Surfactants are contained in the consumer products according to the present invention, i.e. in particular washing agents, in quantitative proportions by preference from 5 wt % to 50 wt %, in particular from 8 wt % to 30 wt %. In laundry post-treatment agents in particular, by preference up to 30 wt %, in particular 5 wt % to 15 wt % surfactants are used, among them preferably cationic surfactants at least in part.

A consumer product according to the present invention by preference contains at least one water-soluble and/or water-insoluble, organic and/or inorganic builder. Included among the water-soluble organic builder substances are polycarboxylic acids, in particular citric acid and sugar acids, monomeric and polymeric aminopolycarboxylic acids, in particular methylglycinediacetic acid, nitrilotriacetic acid, and ethylenediaminetetraacetic acid, as well as polyaspartic acid, polyphosphonic acids, in particular aminotris(methylenephosphonic acid), ethylenediaminetetrakis(methylenephosphonic acid), and 1-hydroxyethane-1,1-diphosphonic acid, polymeric hydroxy compounds such as dextrin, as well as polymeric (poly)carboxylic acids, polymeric acrylic acids, methacrylic acids, maleic acids, and mixed polymers thereof, which can also contain, polymerized into them, small proportions of polymerizable substances having no carboxylic-acid functionality. The relative molecular weight of the homopolymers of unsaturated carboxylic acids is generally between 5000 and 200,000, that of the copolymers between 2000 and 200,000, by preference 50,000 to 120,000, based in each case on free acid. A particularly preferred acrylic acid-maleic acid copolymer has a relative molecular weight from 50,000 to 100,000. Suitable (although less preferred) compounds of this class are copolymers of acrylic acid or methacrylic acid with vinyl ethers, such as vinyl methyl ethers, vinyl esters, ethylene, propylene, and styrene, in which the proportion of acid is equal to at least 50 wt %.

Organic builder substances can be contained if desired in quantities of up to 40 wt %, in particular up to 25 wt %, and by preference from 1 wt % to 8 wt %. Quantities close to the aforesaid upper limit are used by preference in pasty or liquid, in particular water-containing, consumer products according to the present invention. Consumer products such as laundry post-treatment agents, for example fabric softeners, according to the present invention can also, if applicable, be free of organic builder.

Possibilities as water-soluble inorganic builder materials are, in particular, alkali silicates and polyphosphates, by preference sodium triphosphate. Crystalline or amorphous alkali aluminosilicates are used in particular as water-insoluble, water-dispersible inorganic builder materials, in quantities of e.g. up to 50 wt %, by preference not above 40 wt %, and in liquid agents in particular from 1 wt % to 5 wt %, in the consumer products according to the present invention. Among these, the crystalline sodium aluminosilicates of washing-agent quality, in particular zeolite A, P, and if applicable X, are preferred. Quantities close to the aforesaid upper limit are used by preference in solid, particulate agents. Suitable aluminosilicates comprise, in particular, no particles having a particle size greater than 30 μm, and by preference are made up at a proportion of at least 80 wt % of particles having a size less than 10 μm.

Suitable substitutes respectively partial substitutes for the aforesaid aluminosilicate are crystalline alkali silicates, which can be present alone or mixed with amorphous silicates. The alkali silicates usable in the consumer products according to the present invention as builders have by preference a molar ratio of alkali oxide to $SiO_2$ below 0.95, in particular from 1:1.1 to 1:12, and can be present in amorphous or crystalline fashion.

Builder substances are contained in the consumer products according to the present invention, if desired, by preference in quantities of up to 60 wt %, in particular from 5 wt % to 40 wt %. Laundry post-treatment agents according to the present invention, for example fabric softeners, according to the present invention are by preference free of inorganic builders.

Peroxygen compounds that are suitable are, in particular, organic peracids respectively peracid salts of organic acids such as phthalimidopercapronic acid, perbenzoic acid, or salts of diperdodecanedioic acid, hydrogen peroxide, and inorganic salts that release hydrogen peroxide under utilization conditions, such as perborate, percarbonate, and/or persilicate. If solid peroxygen compounds are to be used, they can be utilized in the form of powders or granulates, which in principle can also be encased in known fashion. Alkali percarbonate, alkali perborate monohydrate, or (in particular in liquid agents) hydrogen peroxide in the form of aqueous solutions that contain 3 wt % to 10 wt % hydrogen peroxide, are used with particular preference. If a consumer product according to the present invention contains bleaching agents, such as preferably peroxygen compounds, the latter are present in quantities of preferably up to 50 wt %, in particular from 5 wt % to 30 wt %. The addition of small quantities of known bleaching-agent stabilizers, for example phosphonates, borates resp. metaborates, and metasilicates, as well as magnesium salts such as magnesium sulfate, may be useful.

Compounds that, under perhydrolysis conditions, yield aliphatic peroxocarboxylic acids having by preference 1 to 10 carbon atoms, in particular 2 to 4 carbon atoms, and/or (optionally substituted) perbenzoic acid, can be used as bleach activators. Substances that carry the O- and/or N-acyl groups having the aforesaid number of carbon atoms, and/or optionally substituted benzoyl groups, are suitable. Multiply acylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetyl glycoluril (TAGU), N-acylimides, in particular N-nonanoyl succinimide (NOSI), acylated phenolsulfonates, in particular n-nonanoyl or isononanoyl oxybenzenesulfonate (n-resp. iso-NOBS), carboxylic acid anhydrides, in particular phthalic acid anhydride, acylated polyvalent alcohols, in particular triacetin, ethylene glycol diacetate, 2,5-diacetoxy-2,5-dihydrofuran, and enol esters, as well as acetylated sorbitol and mannitol respectively mixtures thereof (SORMAN), acylated sugar derivatives, in particular pentaacetylglucose (PAG), pentaacetylfructose, tetraacetylxylose and octaacetyllactose, as well as acetylated, optionally N-alkylated glutamine and gluconolactone, and/or N-acylated lactams, for example N-benzoylcaprolactam, are preferred. Hydrophilically substituted acyl acetates and acyl lactams are likewise used in preferred fashion. Combinations of conventional bleach activators can also be used. Such bleach activators can be contained in the usual quantity range, by preference in quantities from 1 wt % to 10 wt %, in particular 2 wt % to 8 wt %, based on the total consumer product.

Suitable enzymes usable in the consumer products are those from the class of the proteases, cutinases, amylases, pullulanases, hemicellulases, cellulases, lipases, oxidases, and peroxidases, as well as mixtures thereof. Enzymatic active substances recovered from fungi or bacteria, such as *Bacillus subtilis, Bacillus licheniformis, Streptomyces griseus, Humicola lanuginosa, Humicola insolens, Pseudomonas pseudoalcaligenes,* or *Pseudomonas cepacia*, are particularly suitable. The enzymes that are optionally used can be adsorbed onto carrier substances and/or embedded into encasing substances in order to protect them from premature inactivation. They are contained in the consumer products according to the present invention, in particular washing agents, by preference in quantities not above 5 wt %, in particular from 0.2 wt % to 2 wt %.

The consumer products can contain as optical brighteners, for example, derivatives of diaminostilbenedisulfonic acid resp. alkali metal salts thereof. Suitable, for example, are salts of 4,4'-bis(2-anilino-4-morpholino-1,3,5-triazinyl-6-amino)stilbene-2,2'-disulfonic acid, or compounds of similar structure that carry, instead of the morpholino group, a diethanolamino group, a methylamino group, an anilino group, or a 2-methoxyethylamino group. Brighteners of the substituted diphenylstyryl type can also be present, for example the alkali salts of 4,4'-bis(2-sulfostyryl)diphenyl, of 4,4'-bis(4-chloro-3-sulfostyryl)diphenyl, or of 4-(4-chlorostyryl)-4'-(2-sulfostyryl)diphenyl. Mixtures of the aforesaid brighteners can also be used.

Included among the suitable foam inhibitors are, for example, organopolysiloxanes and mixtures thereof with microfine, optionally silanated silicic acid, as well as paraffin waxes and mixtures thereof with silanated silicic acid or bis-fatty acid alkylenediamides. Mixtures of different foam inhibitors, for example those made of silicones, paraffins, or waxes, are also used with advantage. The foam inhibitors, in particular silicone- and/or paraffin-containing foam inhibitors, are by preference bound to a granular carrier substance that is soluble respectively dispersible in water. Mixtures of paraffins and bistearylethylenediamides are particularly preferred in this context.

In addition, the consumer products can also contain components that positively influence the ability of oils and fats to be washed out of textiles (so-called "soil release active substances"). This effect becomes particularly apparent when the soiled textile is one that has already been previously washed several times with a washing agent according to the present invention that contains this oil- and fat-releasing component. The preferred oil- and fat-releasing components include, for example, nonionic cellulose ethers such as methyl cellulose and methylhydroxypropyl cellulose having a 15 to 30 wt % proportion of methoxyl groups and a 1 to 15 wt % proportion of hydroxypropoxyl groups, based in each case on the nonionic cellulose ethers, as well as polymers, known from the existing art, of phthalic acid and/or terephthalic acid resp. of their derivatives with monomeric and/or polymeric diols, in particular polymers of ethylene terephthalates and/or polyethylene glycol terephthalates or anionically and/or nonionically modified derivatives thereof.

The consumer products can also contain color transfer inhibitors, by preference in quantities from 0.1 wt % to 2 wt %, in particular 0.1 wt % to 1 wt %, which in a preferred embodiment of the invention are polymers of vinylpyrrolidone, vinylimidazole, vinylpyridine-N-oxide, or copolymers thereof. Also usable are both polyvinylpyrrolidones having molecular weights from 15,000 to 50,000 and polyvinylpyrrolidones having molecular weights above 1,000,000, in particular from 1,500,000 to 4,000,000, N-vinylimidazole/N-vinylpyrrolidone copolymers, polyvinyloxazolidones, copolymers based on vinyl monomers and carboxylic acid amides, pyrrolidone-group-containing polyesters and polyamides, grafted polyamidoamines and polyethylenimines, polymers having amide groups made up of secondary amines, polyamine-N-oxide polymers, polyvinyl alcohols, and copolymers based on acrylamidoalkenyl sulfonic acids.

The purpose of anti-gray agents is to keep dirt that has been detached from the textile fibers suspended in the bath. Water-soluble colloids, usually organic in nature, are suitable for this, for example starch, size, gelatin, salts of ethercarboxylic or ethersulfonic acids of starch or of cellulose, or salts of acid sulfuric-acid esters of cellulose or of starch. Water-soluble polyamides containing acid groups are also suitable for this purpose. Starch derivatives other than those recited above can also be used, for example aldehyde starches. Cellulose ethers such as carboxymethyl cellulose (sodium salt), methyl cellulose, hydroxyalkyl cellulose, and mixed ethers such as methylhydroxyethyl cellulose, methylhydroxypropyl cellulose, methylcarboxymethyl cellulose, and mixtures thereof are preferably used, for example in quantities from 0.1 to 5 wt % based on the consumer product.

Included among the organic solvents usable in the consumer products according to the present invention, especially when the latter are present in liquid or pasty form, are alcohols having 1 to 4 carbon atoms, in particular methanol, ethanol, isopropanol, and tert-butanol, diols having 2 to 4 carbon atoms, in particular ethylene glycol and propylene glycol, as well as mixtures thereof, and the ethers derivable from the aforesaid compound classes. Water-miscible solvents of this kind are present in the consumer products according to the present invention, for example washing agents, by preference in quantities not above 30 wt %, in particular from 6 wt % to 20 wt %.

In order to establish a desired pH that does not result of itself from mixture of the other components, the consumer products according to the present invention can contain system-compatible and environmentally compatible acids, in particular citric acid, acetic acid, tartaric acid, malic acid, lactic acid, glycolic acid, succinic acid, glutaric acid, and/or adipic acid, but also mineral acids, in particular sulfuric acid, or bases, in particular ammonium hydroxides or alkali hydroxides. pH regulators of this kind are optionally contained in the consumer products according to the present invention in quantities by preference not above 20 wt %, in particular from 1.2 wt % to 17 wt %.

The manufacture of solid consumer products according to the present invention presents no difficulties and can in principle occur in known fashion, for example by spraydrying or granulation; a peroxygen compound and optional bleach catalyst can, if applicable, be added later. The perfume compositions according to the present invention, as well as optionally further fragrances, are by preference applied onto the consumer product at the end of the manufacturing process. A method comprising an extrusion step is preferred for the manufacture of consumer products according to the present invention having an elevated bulk weight, in particular in the range from 650 g/l to 950 g/l. The manufacture of liquid agents according to the present invention likewise presents no difficulties and can likewise occur in known fashion, the perfume compositions according to the present invention, as well as optionally further fragrances, being by preference introduced into the consumer product (e.g. washing agent) at the end of the manufacturing process.

According to a preferred embodiment, the teaching according to the present invention can be used to significantly reduce the perfume proportion in washing, cleaning, and toiletry agents. As a result, it is possible to offer perfumed products even for those particularly sensitive consumers who, because of specific incompatibilities and irritations, can use normally perfumed products only to a limited extent or not at all. Mention may be made in this connection chiefly of skin care products and deodorants, but also of washing agents such as, for example, hand washing agents.

A preferred consumer product according to the present invention is a solid, in particular powdered, washing agent that by preference can contain, alongside the perfume composition according to the present invention, components that are selected, for example, from the following:
    anionic surfactants such as, by preference, alkylbenzenesulfonate, alkyl sulfate, e.g. in quantities by preference from 5 to 30 wt %,
    nonionic surfactants such as, by preference, fatty alcohol polyglycol ethers, alkylpolyglucoside, fatty acid glucamide, e.g. in quantities by preference from 0.5 to 15 wt %,
    builders such as, for example, zeolite, polycarboxylate, sodium citrate, in quantities from, for example, 0 to 70 wt %, advantageously 5 to 60 wt %, by preference 10 to 55 wt %, in particular 15 to 40 wt %,
    alkalis such as, for example, sodium carbonate, in quantities e.g. from 0 to 35 wt %, advantageously 1 to 30 wt %, by preference 2 to 25 wt %, in particular 5 to 20 wt %,
    bleaching agents such as, for example, sodium perborate, sodium percarbonate, in quantities e.g. from 0 to 30 wt %, advantageously 5 to 25 wt %, by preference 10 to 20 wt %,
    corrosion inhibitors, e.g. sodium silicate, in quantities e.g. from 0 to 10 wt %, advantageously 1 to 6 wt %, by preference 2 to 5 wt %, in particular 3 to 4 wt %,
    stabilizers, e.g. phosphonates, advantageously 0 to 1 wt %,
    foam inhibitor, e.g. soap, silicone oils, paraffins, advantageously 0 to 4 wt %, by preference 6.1 to 3 wt %, in particular 0.2 to 1 wt %,
    enzymes, e.g. proteases, amylases, cellulases, lipases, advantageously 0 to 2 wt %, by preference 0.2 to 1 wt %, in particular 0.3 to 0.8 wt %,
    anti-gray agent, e.g. carboxymethyl cellulose, advantageously 0 to 1 wt %,
    discoloration inhibitor, e.g. polyvinylpyrrolidone derivatives, e.g. 0 to 2 wt %,
    adjusting agent, e.g. sodium sulfate, advantageously 0 to 20 wt %,
    optical brightener, e.g. stilbene derivative, biphenyl derivative, advantageously 0 to 0.4 wt %, in particular 0.1 to 0.3 wt %,
    optionally further fragrances,
    optionally water,
    optionally soap,
    optionally bleach activators,
    optionally cellulose derivatives,
    optionally dirt repellents,
"wt %" being based in each case on the total agent.

In another preferred embodiment of the invention, the consumer product is present in liquid form, by preference in gel form. Preferred liquid washing or cleaning agents have water contents of, for example, 10 to 95 wt %, by preference 20 to 80 wt %, and in particular 30 to 70 wt %, based on the total agent. In the case of liquid concentrates the water content can also be particularly low, e.g. ≤30 wt %, by preference ≤20 wt %, in particular ≤15 wt %, "wt %" being based in each case on the total agent. The liquid consumer products can also contain non-aqueous solvents.

A preferred consumer product according to the present invention is a liquid, in particular gel-type, washing agent that by preference can contain, alongside the perfume composition according to the present invention, components that are selected e.g. from the following:
    anionic surfactants such as, by preference, alkylbenzenesulfonate, alkyl sulfate, e.g. in quantities by preference from 5 to 40 wt %,
    nonionic surfactants such as, by preference, fatty alcohol polyglycol ethers, alkylpolyglucoside, fatty acid glucamide, for example in quantities by preference from 0.5 to 25 wt %,
    builders such as, for example, zeolite, polycarboxylate, sodium citrate, advantageously 0 to 15 wt %, by preference 0.01 to 10 wt %, in particular 0.1 to 5 wt %,
    foam inhibitor, e.g. soap, silicone oils, paraffins, in quantities e.g. from 0 to 10 wt %, advantageously 0.1 to 4 wt %, by preference 0.2 to 2 wt %, in particular 1 to 3 wt %,
    enzymes, e.g. proteases, amylases, cellulases, lipases, in quantities e.g. from 0 to 3 wt %, advantageously 0.1 to 2 wt %, by preference 0.2 to 1 wt %, in particular 0.3 to 0.8 wt %,
    optical brightener, e.g. stilbene derivative, biphenyl derivative, in quantities e.g. from 0 to 1 wt %, advantageously 0.1 to 0.3 wt %, in particular 0.1 to 0.4 wt %,
    optionally further fragrances,
    optionally stabilizers,
    water,
    optionally soap, in quantities e.g. from 0 to 25 wt %, advantageously 1 to 20 wt %, by preference 2 to 15 wt %, in particular 5 to 10 wt %,
    optionally solvents (by preference alcohols), advantageously 0 to 25 wt %, by preference 1 to 20 wt %, in particular 2 to 15 wt %,
"wt %" being based in each case on the total agent.

A preferred consumer product according to the present invention is a liquid fabric softener that by preference can contain, alongside the perfume composition according to the present invention, components that are selected from the following:
    cationic surfactants, such as especially esterquats, e.g. in quantities from 5 to 30 wt %, cosurfactants such as, for example, glycerol monostearate, stearic acid, fatty alcohols, fatty alcohol ethoxylates, e.g. in quantities from 0 to 5 wt %, by preference 0.1 to 4 wt %, emulsifiers such as, for example, fatty amine ethoxylates, e.g. in quantities from 0 to 4 wt %, by preference 0.1 to 3 wt %, optionally further scents, dyes, by preference in the ppm range, stabilizers, by preference in the ppm range, solvents such as, in particular, water, in quantities by preference from 60 to 90 wt %, "wt %" being based in each case on the total agent.

EXAMPLE

Example A

A usual fragrance mixture was incorporated, in usual fashion by being sprayed on, into a previously perfume-free universal powdered washing agent encompassing 15 wt % surfactants (anionic and nonionic surfactants, as well as soap), >30 wt % builders (soda, silicates, zeolites, polymers), 5 wt % oxygen-based bleaching agents. The resulting washing agent was designated washing agent A, and contained a total of 0.3 wt % fragrances.

Example B

A fragrance mixture that differed from the fragrance mixture in Example A only in that it additionally contained methyl serinol was incorporated, likewise in usual fashion by being sprayed on, into a universal powdered washing agent. The resulting washing agent was designated washing agent B, and differed from that of Example A only by the presence of methyl serinol. The fragrance mixture in accordance with Example B was produced by adding 1 part by weight methyl serinol, at room temperature, to the otherwise complete fragrance mixture (100 parts by weight). Stirring was then performed with a magnetic stirrer until the methyl serinol had dissolved.

Storage tests and utilization tests were then carried out using washing agents A and B.

Storage Tests:

For the storage test, the two washing agents were each stored in separate climate chambers for four weeks at 40° C. The scent of the washing agents was then tested by seven perfumers, and the change in scent impression as compared with fresh goods was evaluated. The qualitative change in scent impression was evaluated by each perfumer on a scale using grades from 1 to 5 (5=no detectable change in scent; 4=change in scent just perceptible; 3=change in scent is very small but quickly detectable by the perfumer; 2=slight change in scent; 1=definite change in scent).

After storage, the perfumers scored washing agent A with an average grade of 1.9 (average value for all perfumers over two test runs). Washing agent B, on the other, was graded as 4.0 (average value for all perfumers over two test runs).

Utilization Tests:

After four weeks of storage at 40° C., washing agents A and B were used for washing experiments. White cotton undershirts were washed with each washing agent at the usual dosing ratio. A normal machine wash was carried out at 40° C. in each case. The washed laundry was tested by seven perfumers, in both the wet and dry state, in terms of scent. The perfumers graded on a scale from 1 to 10 (10=excellent performance, meets extraordinary demands; 9=outstanding performance; 8=very good performance; 7=good performance that is considerably above average requirements; 6=still good performance that is still above average requirements; 5=entirely satisfactory, entirely meets average requirements; 4=satisfactory, still meets average requirements; 3 sufficient despite appreciable deficiencies; 2=deficient, considerable deficiencies, does not meet requirements; 1=insufficient, an entirely unusable performance).

The laundry that had been washed with washing agent A, assessed in the wet state, received an average score of 5.0 (average grade of all perfumers over two test runs). The laundry washed with washing agent A, assessed in the dried state (after line drying), received an average score of 3.9 (average grade of all perfumers over two test runs).

The laundry that had been washed with washing agent B, assessed in the wet state, received an average score of 7.2 (average grade of all perfumers over two test runs). The laundry washed with washing agent B, assessed in the dried state (after line drying), received an average score of 7.1 (average grade of all perfumers over two test runs).

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A perfume composition comprising:
one or more fragrance compounds selected from the group of compound classes consisting of terpenoids, pyrocatechol derivatives, phenol derivatives, aromatics, aliphatics, alicycles, and heterocycles;
amino alcohol(s) according to the formula (II)

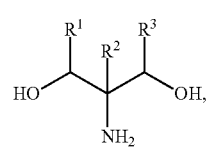

(II)

wherein $R^1$, $R^2$, and $R^3$ in formula (II), mutually independently in each case, denote hydrogen or hydrocarbon residues, or hydroxyalkyl residues in which the hydrocarbon or hydroxyalkyl residues are optionally substituted; and
optionally one or more solvents selected from the group consisting of benzyl alcohol, dipropylene glycol, Dowanol, ethanol, isopropanol, isopropyl myristate, paraffin, propylene glycol, castor oil, and triazine,
wherein the fragrance compound(s) and amino alcohol(s) constitute at least 50 wt. % of the perfume composition.

2. The composition according to claim 1, wherein the formula (II) is selected from the group consisting of 2-aminopropane-1,3-diol, 2-amino-2-(hydroxymethyl)propane-1,3-diol, 2-amino-2-methylpropane-1,3-diol, 2-amino-2-ethylpropane-1,3-diol, and 1-phenyl-2-aminopropane-1,3-diol.

3. The composition according to claim 1, wherein more than 1 wt % of the fragrance compound(s) contained are selected from those fragrances that carry an aldehyde function (RCH=O), a keto group (RR'C=O), a hydroxy function (—OH), and/or groups having isolated double bonds, the "wt %" indication referring to the total quantity of perfume oils contained in the composition.

4. The composition according to claim 1, wherein at least one scent aldehyde selected from adoxal, anisaldehyde, cymal, ethyl vanillin, florhydral, helional, heliotropin, hydroxycitronellal, koavon, lauraldehyde, lyral, methylnonylacetaldehyde, P-T-bucinal, phenylacetaldehyde, undecylenealdehyde, vanillin, 2,6,10-trimethyl-9-undecenal, 3-dodecen-1-al, alpha-n-amylcinnamaldehyde, 4-methoxybenzaldehyde, benzaldehyde, 3-(4-tert-butylphenyl)propanal, 2-methyl-3-(para-methoxyphenyl)propanal, 2-methyl-4-(2,6,6-trimethyl-2(1)-cyclohexen-1-yl)butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzylaldehyde, 1,2,3,4,5,6,7,8-octahydro-8,8-dimethyl-2-naphthaldehyde, 2,4-dimethyl-3-cyclohexene-1-carboxaldehyde, 2-methyl-3-(isopropylphenyl)propanal, 1-decanal, decylaldehyde, 2,6-dimethyl-5-heptenal, 4-(tricyclo[5.2.1.0(2,6)]-decylidene-8)-butanal, octahydro-4,7-methane-1H-indenecarboxaldehyde, 3-ethoxy-4-hydroxybenzaldehyde, para-ethyl-alpha,alpha-dimethylhydrocinnamaldebhyde, alpha-methyl-3,4-(methylenedioxy) hydrocinnanmaldehyde, 3,4-methylenedioxybenzaldehyde, alpha-n-hexylcinnam-aldehyde, m-cymene-7-carboxaldehyde, alpha-methylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexenecarboxaldehyde, 1-dodecanal, 2,4-dimethylcyclohexene-3-carboxaldehyde, 4-(4-hydroxy-4-methylpentyl)-3-cylohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert-butyl)propanal, dihydrocinnamaldehyde, 1-methyl-4-(4-methyl-3-pentenyl)-3-cyclohexene-1-carboxaldehyde, 5- or 6-methoxyhexahydro-4,7-methane indane-1- or -2-carboxaldehyde, 3,7-dimethyloctan–1-al, 1-undecanal, 10-undecen–1-al, 4-hydroxy-3-methoxybenzaldehyde, 1-methyl-3-(4-methylpentyl)-3-cyclohexenecarboxaldehyde, 7-hydroxy-3,7-dimethyloctanal, trans-4-decenal, 2,6-nonadienal, para-tolylacetaldehyde, 4-methylphenylacetaldehyde, 2-methyl-4-(2,6,6-trimethyl–1-cyclohexen-1-yl)-2-butenal, ortho-methoxycinnamaldehyde, 3,5,6-trimethyl-3-cyclohexenecarboxaldehyde, 3,7-dimethyl-2-methylene-6-octenal, phenoxyacetaldehyde, 5,9-dimethyl-4,8-decadicnal, peony aldehyde (6,10-dimethyl-3-oxa-5,9-undecadicn-1-al), hexahydro-4,7-methane indane-1-carboxaldehyde, 2-methyloctanal, alpha-methyl-4-(1-methylethyl)benzeneacetaldehyde, 6,6-dimethyl-2-norpinene-2-propionaldehyde, para-methylphenoxyacetaldehyde, 2-methyl-3-phenyl-2-propen–1-al, 3,5,5-trimethylhexanal, hexahydro-8,8-dimethyl-2-naphthaldehyde, 3-propylbicyclo[2.2.1]-hept-5-ene-2-carbaldehyde, 9-decenal, 3-methyl-5-phenyl-1-pentanal, methylnonylacetaldehyde, hexanal, trans-2-hexenal, 1-p-menthene-q-carboxaldehyde, or mixtures thereof, is contained as the fragrance compound(s).

5. The composition according to claim 1, wherein at least one scent ketone, selected from Buccoxime; isojasmone; methyl-beta-naphthylketone; musk indanone; Tonalid/Musk plus; alpha-damascone, beta-damascone, delta-damascone, isodamascone, damascenone, damarose, methyldihydrojasmonate, menthone, carvone, camphor, fenchone, alpha-ionone, beta-ionone, gamma-methyl (so-called) ionone, fleuramone, dihydrojasmone, cis-jasmone, iso-E-Super®, methylcedrenyl ketone or methyl cedrylone, acetophenone, methylacetophenone, para-methoxyacetophenone, methyl-beta-naphtyl ketone, benzylacetone, benzophenone, para-hydroxyphenylbutanone, celery ketone or livescone, 6-isopropyldecahydro-2-naphthone, dimethyloctenone, frescomenthe, 4-(1-ethoxyvinyl)-3,3,5,5-tetramethylcyclohexanone, methylheptenone, 2-(2-(4-methyl-3-cyclohexen-1-yl)propyl)cyclopentanone, 1-(p-menthen-6(2)yl)-1-propanone, 4-(4-hydroxy-3-methoxyphenyl)-2-butanone, 2-acetyl-3,3-dimethylnorbornane, 6,7-dihydro-1,1,2,3,3-pentamethyl-4(5H)indanone, 4-damascol, dulcinyl or cassione, gelsone, hexalone, isocyclemone E, methylcyclocitrone, methyl lavender ketone, orivone, para-tertiary butylcyclohexanone, verdone, deiphone, muscone, neobutenone, plicatone, veloutone, 2,44,7-tetramethyloct-6-en-3-one, tetrameran, or mixtures thereof, is contained as the fragrance compound(s).

6. The composition according to claim 1, wherein the amino alcohol is included in quantities from 0.001 to 30 wt %.

7. The composition according to claim 1, wherein the composition further comprises <15 wt % surfactants.

8. A method for manufacturing perfumed consumer product(s), comprising:
    adding a perfume composition according to claim 1 to the consumer product(s).

9. A method for stabilizing one or more fragrance compounds, comprising
    adding amino alcohol(s) according to the formula (III)

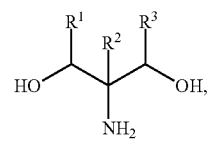

(II)

wherein $R^1$, $R^2$, and $R^3$ in formula (I), mutually independently in each case, denote hydrogen or hydrocarbon residues, or hydroxyalkyl residues in which the hydrocarbon or hydroxyalkyl residues are optionally substituted to a perfume composition comprising one or more fragrance compounds selected from the group of compound classes consisting of terpenoids, pyrocatechol derivatives, phenol derivatives, aromatics, aliphatics, alicycles, and heterocycles, wherein the perfume composition optionally comprises one or more solvents selected from the group consisting of benzyl alcohol, dipropylene glycol, Dowanol, ethanol, isopropanol, isopropyl myristate, paraffin, propylene glycol, castor oil, and triazine, and wherein the fragrance compound(s) and amino alcohol(s) constitute at least 50 wt. % of the perfume composition.

\* \* \* \* \*